United States Patent [19]

Lieb et al.

[11] 4,340,599

[45] Jul. 20, 1982

[54] PHOSPHONO-HYDROXY-ACETIC ACID AND ITS SALTS, THEIR PRODUCTION AND THEIR MEDICINAL USE

[75] Inventors: Folker Lieb, Leverkusen; Hermann Oediger, Cologne; Gert Streible, Wuppertal, all of Fed. Rep. of Germany

[73] Assignee: Bayer Aktiengesellschaft, Leverkusen, Fed. Rep. of Germany

[21] Appl. No.: 190,697

[22] Filed: Sep. 25, 1980

[30] Foreign Application Priority Data

Oct. 12, 1979 [DE] Fed. Rep. of Germany ....... 2941384

[51] Int. Cl.³ .......................... A61K 31/66; C07F 9/38
[52] U.S. Cl. ................................. 424/212; 260/429.9; 260/501.19; 260/501.21; 260/941; 424/199
[58] Field of Search ................... 260/502.4 R; 424/212

[56] References Cited

U.S. PATENT DOCUMENTS

| | | | |
|---|---|---|---|
| 3,032,500 | 5/1962 | Milks et al. ................... | 260/502.4 R |
| 3,159,537 | 12/1964 | Tskosue et al. .............. | 260/502.4 R |
| 3,767,795 | 10/1973 | Schleicher et al. ................. | 424/212 |
| 3,923,876 | 12/1975 | Heins et al. .................. | 260/502.4 R |
| 3,962,433 | 6/1976 | Worms et al. ........................ | 424/212 |
| 3,965,254 | 6/1976 | Tofe et al. .................... | 260/502.4 R |
| 4,016,264 | 4/1977 | Clark ............................ | 260/502.4 R |
| 4,092,412 | 5/1978 | Mao et al. ............................ | 424/212 |
| 4,150,125 | 4/1979 | Herrin et al. ........................ | 424/212 |
| 4,215,113 | 7/1980 | Eriksson et al. ..................... | 424/212 |

*Primary Examiner*—Joseph E. Evans
*Attorney, Agent, or Firm*—Sprung, Horn, Kramer & Woods

[57] ABSTRACT

The invention relates to phosphono-hydroxyacetic acid and salts thereof of Formula I as defined hereinabove, useful as antiviral agents, e.g. antiherpes agents. Also included in the invention are pharmaceutical compositions and medicaments containing said compounds of Formula I as the active ingredients as well as methods for the use of said compounds, compositions and medicaments.

4 Claims, No Drawings

PHOSPHONO-HYDROXY-ACETIC ACID AND ITS SALTS, THEIR PRODUCTION AND THEIR MEDICINAL USE

The present invention relates to phosphono-hydroxyacetic acid and its salts, which are new, to process for their production and to their use as antiviral agents in medicine.

Antiviral agents are already known, for example agents from the nucleoside class of substances which have an action against herpes simplex viruses, such as 5-iodo-2'-desoxy-uridine (see M. Negwer, Organisch-chemische Arzneimittel und ihre Synonyma (Organo-chemical medicaments and their synonymes), page 187, No. 1017; Akademie-Verlag, Berlin 1978). However, they frequently have undesired side effects, such as mutagenic, teratogenic or immuno-suppressive effects.

Moreover, for example, N-(1-adamantyl)-2-(2-dimethyl-aminoethoxy)-acetamide from the aminoadamantane series has been disclosed (see DOS (German Published Specification) 1,941,218). However, compared with known antiviral agents, this compound has only a weak action.

Phosphonoacetic acid has also been disclosed as an antiviral agent. Structure/action relationships show that the antiviral action of phosphonoacetic acid is also linked with the unsubstituted methylene group. (see Pharmacology and Therapeutics, Volume 4, pages 231–243 (1979)).

According to the present invention there are provided compounds which are phosphono-hydroxy-acetic acid of the formula

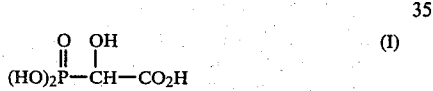

or salts thereof. The novel compounds of the present invention have powerful antiviral properties.

According to the present invention there is further provided a process for the production of a compound of the present invention in which a compound of the formula

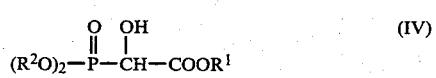

in which
R$^1$ and R$^2$ represent alkyl groups or a benzyl group, (a) in the case where R$^1$ and R$^2$ represent alkyl, is reacted with water in the presence of an acid or, (b), alternatively, in the case where R$^1$ and R$^2$ represents alkyl, after reaction with a silylating reagent in an anhydrous medium, is then reacted with water in the presence of an acid or base; or (c) in the case where R$^1$ and R$^2$ represent benzyl is reacted with hydrogen in the presence of a metal of the eighth auxiliary group as catalyst; and, if desired, the phosphono-hydroxy-acetic acid is thereafter converted into a salt thereof.

Among the new phosphono-hydroxy-acetic acid salts of the invention, those salts that are pharmaceutically acceptable are particularly important and are preferred.

The new free phosphono-hydroxy-acetic acid of the formula (I) and its salts can be interconverted in any suitable manner; methods for such interconversion are known in the art.

The starting compound of formula (IV) may be prepared by reacting an aldehyde of the formula

in which
R$^1$ represents an alkyl or a benzyl group, with a phosphite of the formula

in which
R$^2$ represents an alkyl group if R$^1$ is alkyl or a benzyl group if R$^1$ is benzyl, in the presence of a base.

Reaction variant (b) may, in more detail, be carried out either, (1) by reacting the compound of formula (IV) with a trialkylsilyl halide of the formula

in which
each R$^3$ independently represents an alkyl group, and Hal represents a chlorine, bromine or iodine atom, hydrolysing the product with water and reacting the resulting compound of the formula

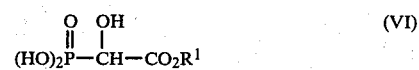

in which
R$^1$ has the above meaning, with water in the presence of an acid or base, or (2) reacting the compound of formula (IV) with a silylating reagent and reacting the resulting compound of the general formula

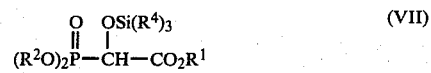

in which
R$^1$ and R$^2$ have the above meaning and
R$^4$ represents alkyl, with a trialkylsilyl halide of the formula (V), as given above, hydrolysing the product with water and reacting the resulting compound with water in the presence of an acid or base.

Surprisingly, the phosphono-hydroxy-acetic acid according to the invention exhibits a considerably more powerful and/or broader antiviral activity than the antiviral active compounds known from the state of the art. The substance according to the invention thus represents an enrichment of pharmacy.

According to the state of the art (see Pharmacology and Therapeutics, Volume 4, pages 231–243 (1979)), a phosphonoacetic acid substituted on the methylene group should display no antiviral action or only a very slight antiviral action. To employ phosphono-hydroxy-acetic acid as an antiviral substance was thus to overcome a scientific prejudice.

If dimethyl phosphite and glyoxylic acid butyl ester are used as starting substances and trimethylsilyl iodide, water and sodium hydroxide solution are used for the saponification, the course of the reaction can be illustrated by Equation B in the reaction scheme which follows.

The glyoxylic acid esters used as starting substances are known (see Organic Synthesis Volume 4, page 124), or they can be prepared by known processes.

In the formula (II), $R^1$ preferably represents and alkyl group with 1 to 8 (more specifically 1 to 4 carbon atoms) carbon atoms, preferably a propyl or butyl group, or a benzyl group.

Examples of compounds of formula (II) which may be mentioned are: glyoxylic acid propyl ester, glyoxylic acid butyl ester and glyoxylic acid benzyl ester.

The dialkyl or diaralkyl phosphites used as starting substances are likewise known (see Houben-Weyl, Methoden der organischen Chemie (Methods of Organic Chemistry), Volume XII/2, page 20).

In the formula (III), $R^2$ preferably represents an alkyl group with 1 to 4 carbon atoms, preferably a methyl or ethyl group, or a benzyl group.

Examples of compounds of formula (III) which may be mentioned are: dimethyl phosphite, diethyl phosphite and dibenzyl phosphite.

Possible diluents are any inert organic solvents. Suitable solvents are aromatic hydrocarbons, such as, toluene; acyclic or cyclic ethers (for example diethyl ether or dioxane); alcohols, such as alkanols preferably having 1 to 3 carbon atoms (for example methanol or ethanol), aliphatic (e.g. $C_1$–$C_4$-alkane) carboxylic acid amides (for example dimethyl formamide), and aliphatic (e.g. $C_1$–$C_4$-alkane) carboxylic acid nitriles (for example acetonitrile). However, the reaction can also be carried out without diluents.

The preparation of compounds according to the invention is illustrated by the following reaction scheme.

The initial reaction of compounds of the formula (II) with those of the formula (III) is carried out in the presence of a base. Alkaline earth metal hydroxides, alkali metal hydroxides or alkali metal alcoholates (such as alkanolates derived from alkanols having 1, 2 or 3 carbon atoms), in particular sodium hydroxide or sodium methylate, are preferably used.

The reaction of compounds of the formula (II) with those of the formula (III) is generally carried out at temperatures between 0° and 150° C., preferably between 25° and 120° C. The reaction time depends on the temperature and is generally between 1 and 30 hours.

In carrying out the reaction of compounds of formula (II) with compounds of formula (III), 1 mole of the compound of formula (II) is generally reacted with 0.9 to 1.1 moles, preferably with 0.95 to 1.0 mole, of the compound of formula (II), 0.01 to 0.1 mole of base being added, to give the compound of the formula (IV).

Starting from compounds of formula (IV), in reaction variant (a) (as illustrated in Equation A of the above reaction scheme), the compounds of the general formula (IV) are saponified under acid conditions. Acids which are used are preferably aqueous inorganic acids, such as mineral acids, for example sulphuric acid or, preferably, hydrochloric acid.

The saponification of (IV) to give phosphonohydroxyacetic acid (I) is generally carried out in a temperature range between 20° and 120° C., preferably between 90° and 110° C.

In general, 1 mol of the compound (IV) is reacted with 5 to 20 mols of acid, preferably with 8 to 15 mols of acid. The reaction time depends on the temperature and is generally between 10 and 20 hours.

The reaction variant (b) for the preparation of phosphono-hydroxyacetic acid of formula (I) comprises reacting a phosphono ester of the formula (IV) with a trialkylsilyl halide of the formula (V) (as illustrated previously as Equation B of the reaction scheme).

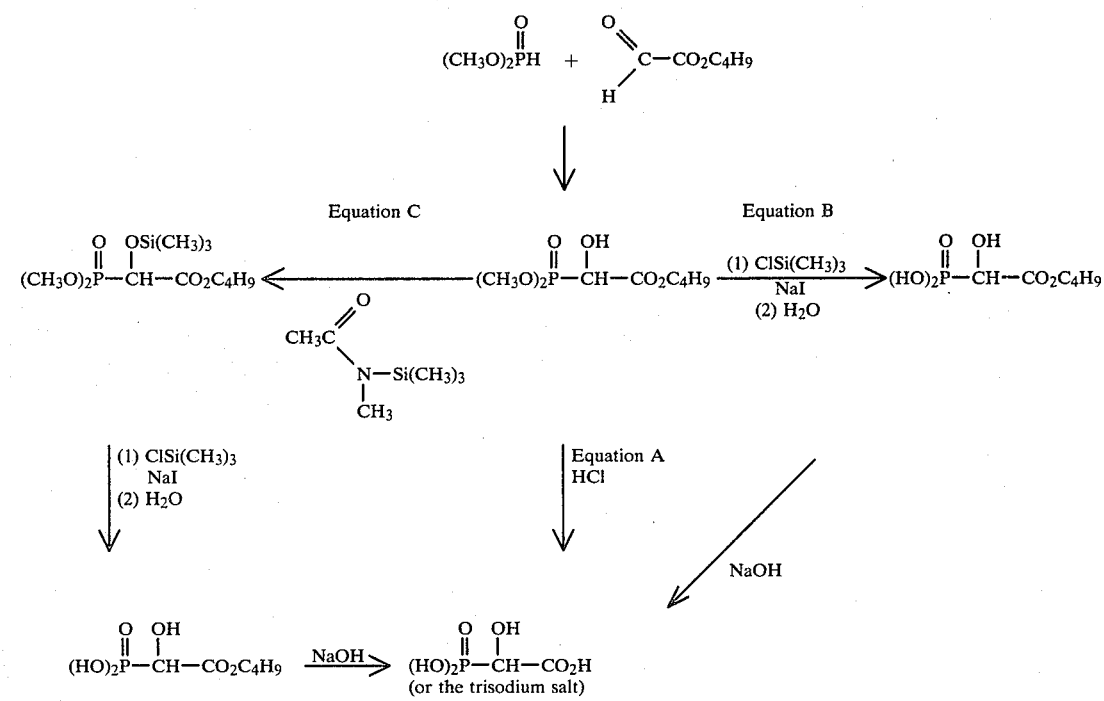

The trialkylsilyl halide (V) used as starting substances for this variant are likewise known.

In the formula (V), $R^3$ preferably represents an alkyl group with 1 to 4 carbon atoms, it being possible for the alkyl groups to be identical or different, in particular methyl group, Hal represents a chlorine, bromine or iodine atom, especially an iodine atom if $R^3$ represents an ethyl group.

It is not necessary to add the trialkylsilyl iodides as such. It is sufficient to prepare these compounds in situ from the corresponding trialkylsilyl chlorides and sodium iodide in the presence of the phosphono ester of the formula (IV).

Possible diluents for the reaction of compounds of the formula (IV) with those of the formula (V) are inert organic solvents. Suitable solvents are hydrocarbons, such as halogenated hydrocarbons (for example carbon tetrachloride), aromatic hydrocarbons (for example toluene), or alkanecarboxylic acid nitriles with 2 to 4 carbon atoms (for example propionitrile or, preferably acetonitrile).

The reaction of compounds of formula (IV) with compounds of formula (V) is generally carried out in a temperature range between $+10°$ C. and $+80°$ C., preferably between $+20°$ C. and $+70°$ C.

In general, 1 mole of the compound of formula (IV) is generally reacted with 3.0 to 4.0, preferably with 3.0 to 3.2, moles of the compound of formula (V). A larger excess of the compound of formula (V) can also be employed.

The reaction time for the reaction of the compound of formula (IV) with the compound of formula (V) depends on the temperature and on the starting compound employed and is between 15 minutes and 3 hours.

As illustrated in Equation B of the reaction scheme, the silyl ester of the compound of the general formula (IV) is reacted with water.

The reaction of the silyl ester of formula (VI) with water is generally carried out in a temperature range between 0° and 40° C., preferably between 20° and 30° C.

In general, 1 mole of the silyl ester of the compound (VI) is reacted with at least 3 moles of water, and appropriately with a larger excess of about 30 moles of water.

The reaction time depends of the temperature and on the structure of the silyl group and is in general between 1 minute and 10 minutes.

The resulting compound of the general formula (VI) is in general isolated in the form of its alkali or alkaline earth metal salts, for example, the lithium salt or sodium salt, for example, by adding a sufficient amount of aqueous lithium hydroxide solution or sodium hydroxide solution and evaporating the mixture.

The variant (b) for the preparation of phosphonohydroxyacetic acid of formula (I) may alternatively comprise reacting a compound of the general formula (IV) with a silylating reagent to give the compound of formula (VII), in which $R^4$ preferably represents an alkyl group with 1 to 4 carbon atoms, preferably an ethyl group and, especially a methyl group.

Suitable silylating reagents are, above all, those silyl compounds which, after the silyl group has been transferred to the compound of formula (IV), are inert to other reactants in the subsequent course of the sequence of stages, so that isolation is unnecessary. Such compounds include, for example, mono- or bis-silylated lower alkanecarboxylic acid amides, such as N,O-bis-trimethylsilylacetamide or N-trimethylsilyl-N-methylacetamide or N-trimethylsilylacetamide, in particular N-trimethylsilyl-N-methyl-acetamide.

Possible diluents for the reaction of formula (IV) with the silylating reagent are, above all, organic solvents which are inert towards the reactants. Suitable solvents are, above all, hydrocarbons or substituted hydrocarbons, such as halogenated hydrocarbons (for example carbon tetrachloride or chloroform), aromatic hydrocarbons (for example toluene), cyclic ethers (for example tetrahydrofurane or dioxane), or alkanecarboxylic acid nitriles with 1 to 4 carbon atoms (for example propionitrile or preferably, acetonitrile).

The reaction of (IV) with the silylating reagent is generally carried out in a temperature range between $+20°$ and $+80°$ C., preferably between $+30°$ and $+70°$ C.

In general, 1 mol of the compound (IV) is reacted with 1 to 3 mols of silylating reagent, preferably with 1 to 2 mols. A larger excess does no harm.

The reaction time depends on the temperature and is generally between 15 minutes and 5 hours.

It is not necessary to isolate the compound of formula (VII), for example by evaporating off the diluent; the compound can be further reacted directly in the suitable diluent.

As illustrated in Equation C of the reaction scheme, the resulting compound of the formula (VII) is then reacted with a trialkylsilyl halide of the formula (V), corresponding to the second stage in Equation B of the reaction scheme, and the resulting silylated phosphonoacetic acid ester is reacted with water, corresponding to the second stage in Equation B, and isolated in the form of its salts, for example in the form of its alkali metal salts, for example by adding a sufficient amount of aqueous alkali metal, e.g. sodium hydroxide solution and evaporating the mixture.

According to Equations B and C, in the last stage of the process, the compound of the general formula (VI) is saponified. The saponification of the compound of formula (VI) can take place under acid or alkaline conditions.

Aqueous inorganic acids, for example sulphuric acid or, preferably, hydrochloric acid, are used in the acid saponification of the compound of formula (VI). Aqueous sodium hydroxide solution or potassium hydroxide solution, preferably sodium hydroxide solution, are used as bases in the alkaline saponification.

If the compound (VI) is saponified under alkaline conditions, the process according to the invention is generally carried out in a temperature range from 0° to 100° C., preferably from 20° to 40° C. The saponification in an acid medium is generally carried out at 20° to 120°, preferably between 90° and 120° C.

In general 1 mol of the compound (VI) is reacted with 2 to 7 mols of acid, preferably with 4 to 6 mols, or with 3 to 5 mols of alkali, preferably with 3 to 3.5 moles.

The reaction time depends on the temperature and is generally between 5 and 24 hours.

According to reaction variant (c), the compound of the formula (IV) in which $R^1$ and $R^2$ represent benzyl, is split hydrogenolytically in the presence of a metal of the eighth anxiliary group.

Finely divided palladium is a particularly suitable metal.

Possible diluents are, above all, organic solvents which are inert towards the reactants. Suitable solvents are, above all, aliphatic esters (particularly alkyl esters of alkanoic acids with 3 to 8 carbon atoms, such as ethyl acetate.

The process according to the invention is generally carried out in a temperature range from +20° C. to +150° C., preferably between +30° C. and +100° C.

The reaction can be carried out under normal pressure or also under increased pressure. In the latter case, it is in general carried out under pressures between 2 and 100 bars, preferably between about 5 and 50 bars.

The resulting phosphono-hydroxy-acetic acid of the formula (I) is isolated, for example, in the form of its salts, such as its alkali or alkaline earth metal salts, for example, by adding a sufficient amount of aqueous sodium hydroxide solution and evaporating the mixture. The phosphono-hydroxy-acetic acid according to the invention has an action against herpes viruses of human beings and animals in particular against human herpes simplex viruses type 1 and type 2.

The new active compound can be employed as such or in the form of its physiologically acceptable salts, for example salts with organic amines, such as triethylamine, cyclohexylamine or triethanolamine, or salts with inorganic cations, for example, lithium, sodium, potassium, magnesium, calcium, zinc or ammonium to provide alkali or alkaline earth group salts or other metal salts.

As stated above, the invention also relates to the use in medicine of the compounds of the invention.

The present invention provides a pharmaceutical composition containing as active ingredient a compound of the invention in admixture with an inert pharmaceutical carrier, such as a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution, e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters (e.g. $C_{14}$-alcohol with $C_{16}$-fatty acid) or mixtures of these diluents.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example ground nut oil), glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.1 to 10% of the active ingredient by weight of the total composition, preferably as aqueous solutions, for example buffered solutions with a pH of 6 to 8.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include, as wet carriers, solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The production of the above-mentioned pharmaceutical compositions and medicaments is carried out by any method known in the art, for example, by mixing the active ingredient(s) with the diluent(s), i.e. inert carrier(s) to form a pharmaceutical composition (e.g. a granulate) and then forming the composition into the medicament (e.g. tablets).

This invention further provides a method of combating the above-mentioned diseases in warm blooded animals, which comprises administering to the animals a compound of the invention alone or in admixture with a diluent or in the form of a medicament according to the invention.

It is envisaged that these active compounds will be administered perorally, parenterally (for example intraperitoneally) or rectally, parenterally or orally. Preferred pharmaceutical compositions and medicaments are therefore those adapted for administration such as local, parenteral or oral administration. Administration in the method of the invention is preferably parenteral or oral administration.

In general it has proved advantageous to administer amounts of from 10 mg to 1,000 mg/kg of body weight per day to achieve effective results. It has been found, for example, that phosphono-hydroxyacetic acid is effective at a dose range of 50 mg/kg to 500 mg/kg of body weight in mice intraperitoneally infected with herpes simplex virus according to Lopez L. (Nature, London, Vol. 258, p. 152, 1975). Nevertheless, it can at times be necessary to deviate from thos dosage rates, and in particular to do so as a function of the nature and body weight of the subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

The following Examples 1, 3, 5, 7 and 9 illustrate the production of precursors and Examples 2, 4, 6, 8 and 10 illustrate the production of compounds of the present invention.

EXAMPLE 1

Dimethoxyphosphinyl-hydroxy-acetic acid butyl ester 1.5 ml of a saturated methanolic sodium hydroxide solution are allowed to run rapidly into 22 g of dimethyl phosphite and 26 g of glyoxylic acid butyl ester. The reaction which proceeds is highly exothermic. The mixture is subsequently stirred at 25° for some hours and worked up by distillation to give 33.6 g of dimethoxyphosphinylhydroxy-acetic acid butyl ester (yield: 70%). Boiling point $_{0.05}$: 75°–82° C. (thin film evaporator). $^1$H-NMR (CDCl$_3$): $\delta=0.93$ (3H, t, J=5 Hz, CH$_3$), 3.86 (6H, d, J=11 Hz, CH$_3$O), 4.23 (2H, t, J=6 Hz, OCH$_2$) and 4.63 ppm (1H, d, J=18 Hz, P-CH)

EXAMPLE 2

Phosphono-hydroxy-acetic acid 27 g of dimethoxyphosphinyl-hydroxy-acetic acid butyl ester and 200 ml of 5 N hydrochloric acid are boiled under reflux for 15 hours. The water is distilled off, the product is freed from residual water by azeotropic distillation with toluene and 15.0 g of phosphono-hydroxy-acetic acid are obtained (yield: 85%). $^1$H-NMR (D$_2$O): $\delta=4.56$ ppm (1H, d, J=18 Hz, P—CH)

EXAMPLE 3

The disodium salt of phosphono-hydroxy-acetic acid butyl ester 15 g of sodium iodide and 12.0 g of dimethoxyphosphinyl-hydroxy-acetic acid butyl ester are initially introduced into 100 ml of acetonitrile, 16.2 g of trimethylchlorosilane are allowed to run in at 25° C., whilst cooling, and the mixture is then stirred at 25° C. for 2 hours and at 40° C. for 15 minutes. The sodium chloride is removed by filtration or centrifugation and the solution is evaporated in vacuo. The residue thus obtained is taken up in 30 ml of water, neutralised with dilute sodium hydroxide solution and then evaporated in vacuo. After digesting the residue in acetone, 12.2 g of the disodium salt of phosphono-hydroxy-acetic acid butyl ester are obtained. Yield: 95%

$^1$H-NMR (D$_2$O): $\delta=0.93$ (3H, t, J=5 Hz, CH$_2$), 4.23 (2H, t, J=6 Hz, OCH$_2$) and 4.63 ppm (1H, d, J=17 Hz).

EXAMPLE 4

The trisodium salt of phosphono-hydroxy-acetic acid 17 g of the disodium salt of phosphono-hydroxyacetic acid butyl ester are dissolved in 60 ml of water, and 2.6 g of sodium hydroxide are added. The mixture is stirred at 20° for 24 hours. It is evaporated, and 14.6 g of the trisodium salt of phosphono-hydroxyacetic acid are obtained. Yield: 98%

$^1$H-NMR (D$_2$O): $\delta=4.07$ ppm (1H, d, J=18 Hz, P-CH).

EXAMPLE 5

The disodium salt of phosphono-hydroxy-acetic acid butyl ester 7.2 g of N-trimethylsilyl-N-methylacetamide in 20 ml of acetonitrile are allowed to run into a solution of 12 g of dimethoxyphosphinyl-hydroxy-acetic acid butyl ester in 50 ml of acetonitrile at 25°. The mixture is then warmed to 60° C. for 4 hours. 15 g of sodium iodide are added at 25° C. and 10.8 g of trimethylchlorosilane are allowed to run in at 25° C., whilst cooling. The procedure followed is otherwise as described under Example 3. 9.6 g of the disodium salt of phosphonohydroxy-acetic acid butyl ester are obtained. Yield: 75%

EXAMPLE 6

Phosphono-hydroxy-acetic Acid

The reaction of the disodium salt of phosphonohydroxy-acetic acid butyl ester with an aqueous NaOH solution is carried out analogously to Example 4. The trisodium salt of phosphono-hydroxy-acetic acid, obtained is converted into the free phosphonohydroxyacetic acid with the appropriate amount of acid.

EXAMPLE 7

Dibenzyloxyphosphinyl-hydroxy-acetic acid benzyl ester 1.5 ml of a saturated methanolic sodium hydroxide solution are allowed to run rapidly into 45.5 g of dibenzyl phosphite and 28.5 g of glyoxylic acid benzyl ester. The reaction which proceeded is exothermic. The mixture is subsequently stirred at 20° C. for some hours. It is chromatographed on silica gel using methylene chloride containing 5% of methanol. The fraction with a $R_f$ of 0.58 is evaporated, 20 ml of diethyl ether are added to the residue (55.2 g) and 45.0 g of dibenzyloxyphosphinylhydroxy-acetic acid benzyl ester are isolated. Melting point 67°–68° C. Yield: 61%.

EXAMPLE 8

The trisodium salt of phosphono-hydroxy-acetic acid 4.3 g of dibenzyloxyphosphinyl-hydroxy-acetic acid benzyl ester are initially introduced into 150 ml of ethyl acetate, 1 g of palladium-on-charcoal (5% strength) are added and hydrogenation is carried out under normal pressure and at 20° C. After the theoretical amount of hydrogen has been taken up, the catalyst is separated off, the reaction mixture is evaporated in vacuo, the residue is taken up in 15 ml of water and the aqueous mixture is adjusted to pH 8 with 2 N sodium hydroxide solution and evaporated again to dryness in vacuo. 2.2 g of the trisodium salt of phosphonohydroxy-acetic acid are obtained (yield: quantitative). IR (KBr): $\nu=970$, 1,080, 1,405 and 1,590 cm$^{-1}$.

EXAMPLE 9

The dilithium salt of phosphono-hydroxy-acetic acid butyl ester

The procedure followed is as described in Example 3. Neutralisation is carried out with 2 N lithium hydroxide solution instead of with dilute sodium hydroxide solution. The dilithium salt of phosphonohydroxy-acetic acid butyl ester precipitate (yield: 85%). IR (KBr): $\nu=1,710$ cm$^{-1}$.

EXAMPLE 10

The trilithium salt of phosphono-hydroxy-acetic acid 20 ml of water are added to 22 g of the dilithium salt of phosphono-hydroxy-acetic acid butyl ester, and 2.4 g of lithium hydroxide solution are added. The mixture is stirred at 20° for 48 hours. It is evaporated and, after washing with ethanol, 14 g of the trilithium salt of phosphono-hydroxy-acetic acid are obtained (yield: 80%). IR (KBr): $\nu=985$, 1,110, 1,425 and 1,600 cm$^{-1}$ The present invention also comprises pharmaceutically acceptable bioprecursors of the active compounds of the present invention.

For the purpose of this specification the term 'pharmaceutically acceptable bioprecursor' of an active compound of the invention means a compound having a structural formula different from the active compound but which nonetheless, upon administration to a warm-blooded animal is converted in the patient's body to the active compound.

What is claimed is:

1. A method of combating viral infections in warmblooded animals which comprises administering to the animals an antivirally effective amount of a phosphononhydroxy-acetic acid compound of the formula

either alone or in admixture with an inert pharmaceutical carrier or in the form of a medicament.

2. A method according to claim 1 in which the active compound is administered in an amount of 10 to 1,000 mg per kg body weight per day.

3. A method according to claim 1 or 2 in which the active compound is administered parenterally or orally.

4. A method according to claim 1, 2 or 3 in which the viral infection is an infection with herpes viruses.

* * * * *